(12) United States Patent
Okoniewski

(10) Patent No.: US 8,353,874 B2
(45) Date of Patent: Jan. 15, 2013

(54) ACCESS APPARATUS INCLUDING INTEGRAL ZERO-CLOSURE VALVE AND CHECK VALVE

(75) Inventor: Gregory Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 15 days.

(21) Appl. No.: 13/004,057

(22) Filed: Jan. 11, 2011

(65) Prior Publication Data

US 2011/0202008 A1 Aug. 18, 2011

Related U.S. Application Data

(60) Provisional application No. 61/305,635, filed on Feb. 18, 2010.

(51) Int. Cl.
*A61M 5/178* (2006.01)
(52) U.S. Cl. .................................. 604/167.03
(58) Field of Classification Search ............ 604/167.03, 604/167.01, 167.08
See application file for complete search history.

(56) References Cited

U.S. PATENT DOCUMENTS

| | | | |
|---|---|---|---|
| 2,328,948 A * | 9/1943 | Bourke | 217/103 |
| 4,169,474 A | 10/1979 | Wagner | |
| 4,653,539 A | 3/1987 | Bell | |
| 4,655,752 A * | 4/1987 | Honkanen et al. | 604/256 |
| 4,772,273 A | 9/1988 | Alchas | |
| 4,793,351 A | 12/1988 | Landman et al. | |
| 5,098,405 A | 3/1992 | Peterson et al. | |
| 5,102,395 A | 4/1992 | Cheer et al. | |
| 5,141,501 A | 8/1992 | Atkinson et al. | |
| 5,330,436 A | 7/1994 | Heidmueller | |
| 5,342,329 A | 8/1994 | Croquevielle | |
| 5,350,362 A | 9/1994 | Stouder, Jr. | |
| 5,356,394 A | 10/1994 | Farley | |
| 5,374,253 A | 12/1994 | Burns, Sr. et al. | |
| 5,383,860 A | 1/1995 | Lau | |
| 5,391,153 A * | 2/1995 | Haber et al. | 604/167.01 |
| 5,397,314 A | 3/1995 | Farley et al. | |
| 5,403,284 A | 4/1995 | Gross | |
| 5,407,437 A | 4/1995 | Heimreid | |
| 5,441,486 A | 8/1995 | Yoon | |

(Continued)

FOREIGN PATENT DOCUMENTS

DE 20 2006 017791 U1 1/2007

(Continued)

OTHER PUBLICATIONS

European Search Report for corresponding EP112501835 date of mailing is Jun. 8, 2011 (3 pages).

*Primary Examiner* — Nicholas Lucchesi
*Assistant Examiner* — Diva K Chander

(57) ABSTRACT

An access apparatus for use in surgical procedures is provided. The access apparatus includes a zero-closure valve disposed within a housing associated with the access apparatus and adjacent a longitudinal passage defined by an access member operably associated with the access apparatus. The zero-closure valve is configured to provide a substantially fluid-tight seal in the absence of the surgical instrument inserted therethrough. A check-valve is operably associated with the zero-closure valve and is in fluid communication with the longitudinal passage and an insufflation port operably associated with the access member. The check-valve is configured to provide a fluid-tight seal when a pressure inside the access apparatus is greater than a pressure external thereof.

12 Claims, 3 Drawing Sheets

U.S. PATENT DOCUMENTS

| | | | |
|---|---|---|---|
| 5,458,640 A | 10/1995 | Gerrone | |
| 5,496,280 A | 3/1996 | Vandenbroek et al. | |
| 5,535,785 A | 7/1996 | Werge et al. | |
| 5,545,150 A | 8/1996 | Danks et al. | |
| 5,613,954 A | 3/1997 | Nelcon et al. | |
| 5,676,657 A | 10/1997 | Yoon | |
| 5,685,854 A | 11/1997 | Green et al. | |
| 5,707,356 A | 1/1998 | Paul | |
| 5,720,759 A * | 2/1998 | Green et al. | 606/167 |
| 5,820,606 A | 10/1998 | Davis et al. | |
| 5,827,228 A * | 10/1998 | Rowe | 604/167.02 |
| 5,860,947 A | 1/1999 | Stamler | |
| 5,895,377 A * | 4/1999 | Smith et al. | 604/256 |
| 5,899,882 A | 5/1999 | Waksman et al. | |
| 5,928,249 A | 7/1999 | Saadat et al. | |
| 5,989,211 A | 11/1999 | Schaumann et al. | |
| 5,989,228 A | 11/1999 | Danks et al. | |
| 6,017,327 A | 1/2000 | Wiklund | |
| 6,042,586 A | 3/2000 | Kawano et al. | |
| 6,066,117 A | 5/2000 | Fox et al. | |
| 6,083,189 A | 7/2000 | Gonon et al. | |
| 6,083,205 A | 7/2000 | Bourne et al. | |
| 6,086,562 A | 7/2000 | Jacobsen et al. | |
| 6,093,176 A | 7/2000 | Dennis | |
| 6,095,997 A | 8/2000 | French et al. | |
| 6,123,689 A | 9/2000 | To et al. | |
| 6,224,567 B1 | 5/2001 | Roser | |
| RE37,357 E | 9/2001 | Lynn | |
| 6,428,520 B1 | 8/2002 | Lopez et al. | |
| 6,458,103 B1 | 10/2002 | Albert et al. | |
| 6,497,686 B1 | 12/2002 | Adams et al. | |
| 6,497,716 B1 | 12/2002 | Green et al. | |
| 6,569,120 B1 * | 5/2003 | Green et al. | 604/167.04 |
| 6,652,492 B1 | 11/2003 | Bell et al. | |
| 6,685,665 B2 | 2/2004 | Booth et al. | |
| 6,692,467 B2 | 2/2004 | McFarlane | |
| 6,695,810 B2 | 2/2004 | Peacock, III et al. | |
| 6,695,822 B2 | 2/2004 | Adams et al. | |
| 6,726,663 B1 | 4/2004 | Dennis | |
| 6,767,340 B2 * | 7/2004 | Willis et al. | 604/256 |
| 6,786,887 B2 | 9/2004 | Roychowdhury et al. | |
| 6,884,230 B1 | 4/2005 | Epstein et al. | |
| 6,902,535 B2 | 6/2005 | Eberhart et al. | |
| 6,962,575 B2 | 11/2005 | Tal | |
| 6,991,621 B2 | 1/2006 | Bacher et al. | |
| 7,004,914 B2 | 2/2006 | Eberhart et al. | |
| 7,033,339 B1 | 4/2006 | Lynn | |
| 7,052,481 B2 | 5/2006 | Fawcett | |
| 7,097,632 B2 | 8/2006 | Shia et al. | |
| 7,163,525 B2 | 1/2007 | Franer | |
| 7,172,572 B2 | 2/2007 | Diamond et al. | |
| 7,182,752 B2 | 2/2007 | Stubbs et al. | |
| 7,192,433 B2 | 3/2007 | Osypka et al. | |
| 7,226,411 B2 | 6/2007 | Akiba | |
| 7,285,112 B2 | 10/2007 | Stubbs et al. | |
| 7,344,519 B2 | 3/2008 | Wing et al. | |
| 7,371,227 B2 | 5/2008 | Zeiner | |
| 7,390,316 B2 | 6/2008 | McFarlane | |
| 7,390,317 B2 | 6/2008 | Taylor et al. | |
| 7,413,559 B2 | 8/2008 | Stubbs et al. | |
| 7,470,255 B2 | 12/2008 | Stearns et al. | |
| 7,470,261 B2 | 12/2008 | Lynn | |
| 7,484,709 B2 | 2/2009 | Efinger et al. | |
| 7,597,701 B2 * | 10/2009 | Hueil et al. | 606/185 |
| 7,717,878 B2 * | 5/2010 | Smith | 604/167.06 |
| 7,833,199 B2 * | 11/2010 | Franer et al. | 604/167.03 |
| 7,988,671 B2 * | 8/2011 | Albrecht et al. | 604/167.01 |
| 8,034,032 B2 * | 10/2011 | Voegele et al. | 604/167.03 |
| 2001/0016704 A1 | 8/2001 | Zadno-Azizi et al. | |
| 2002/0019609 A1 | 2/2002 | McFarlane | |
| 2002/0110484 A1 | 8/2002 | McIntosh | |
| 2002/0128603 A1 * | 9/2002 | Booth et al. | 604/164.01 |
| 2002/0128660 A1 | 9/2002 | Bidoia | |
| 2002/0133117 A1 | 9/2002 | Zando-Azizi et al. | |
| 2002/0169408 A1 | 11/2002 | Beretta et al. | |
| 2003/0023201 A1 | 1/2003 | Aboul-Hosn et al. | |
| 2003/0093101 A1 | 5/2003 | O'Heeron et al. | |
| 2003/0163115 A1 | 8/2003 | Gershowitz | |
| 2003/0167040 A1 | 9/2003 | Bacher et al. | |
| 2003/0208104 A1 | 11/2003 | Carrillo, Jr. et al. | |
| 2004/0049157 A1 | 3/2004 | Plishka et al. | |
| 2004/0102761 A1 | 5/2004 | Ahmed | |
| 2004/0171979 A1 | 9/2004 | O'Neil | |
| 2004/0171990 A1 | 9/2004 | Dennis et al. | |
| 2004/0176744 A1 | 9/2004 | Lange et al. | |
| 2004/0220522 A1 | 11/2004 | Briscoe et al. | |
| 2004/0236347 A1 | 11/2004 | Karasawa | |
| 2004/0243059 A1 | 12/2004 | Pajunk et al. | |
| 2005/0015043 A1 | 1/2005 | Stubbs et al. | |
| 2005/0059934 A1 * | 3/2005 | Wenchell et al. | 604/167.01 |
| 2005/0070850 A1 | 3/2005 | Albrecht | |
| 2005/0070851 A1 * | 3/2005 | Thompson et al. | 604/167.03 |
| 2005/0085792 A1 | 4/2005 | Gershowitz | |
| 2005/0092662 A1 | 5/2005 | Gilbert et al. | |
| 2005/0096591 A1 | 5/2005 | Dion et al. | |
| 2005/0113757 A1 | 5/2005 | McFarlane | |
| 2005/0124932 A1 * | 6/2005 | Foster et al. | 604/99.04 |
| 2005/0131344 A1 | 6/2005 | Godaire | |
| 2005/0131349 A1 * | 6/2005 | Albrecht et al. | 604/167.06 |
| 2005/0192537 A1 | 9/2005 | Osborne et al. | |
| 2005/0209580 A1 | 9/2005 | Freyman | |
| 2005/0288634 A1 * | 12/2005 | O'Heeron et al. | 604/167.06 |
| 2006/0069352 A1 | 3/2006 | Eisenkolb et al. | |
| 2006/0135972 A1 | 6/2006 | Zeiner | |
| 2006/0135977 A1 | 6/2006 | Thompson et al. | |
| 2006/0135978 A1 | 6/2006 | Franer | |
| 2006/0149294 A1 | 7/2006 | Argentine et al. | |
| 2006/0161102 A1 | 7/2006 | Newcomb et al. | |
| 2006/0167438 A1 | 7/2006 | Kalser et al. | |
| 2006/0178648 A1 | 8/2006 | Barron et al. | |
| 2006/0184091 A1 | 8/2006 | Dimalanta et al. | |
| 2006/0195057 A1 | 8/2006 | Kriesel et al. | |
| 2006/0220325 A1 * | 10/2006 | McFarlane | 277/607 |
| 2006/0229564 A1 | 10/2006 | Anderson et al. | |
| 2006/0253077 A1 * | 11/2006 | Smith | 604/167.06 |
| 2007/0005001 A1 | 1/2007 | Rowe et al. | |
| 2007/0073241 A1 | 3/2007 | Sauer et al. | |
| 2007/0078395 A1 | 4/2007 | Valaie | |
| 2007/0078397 A1 | 4/2007 | Weststrate | |
| 2007/0088275 A1 | 4/2007 | Stearns et al. | |
| 2007/0088277 A1 * | 4/2007 | McGinley et al. | 604/167.01 |
| 2007/0118068 A1 | 5/2007 | Hawkins | |
| 2007/0135751 A1 | 6/2007 | DiCarlo et al. | |
| 2007/0135752 A1 | 6/2007 | Domash et al. | |
| 2007/0173777 A1 | 7/2007 | Murphy | |
| 2007/0181483 A1 | 8/2007 | Tonelli et al. | |
| 2007/0197954 A1 | 8/2007 | Keenan | |
| 2007/0255218 A1 * | 11/2007 | Franer | 604/167.02 |
| 2007/0260186 A1 | 11/2007 | Lang | |
| 2007/0282250 A1 | 12/2007 | Anderson et al. | |
| 2007/0282268 A1 | 12/2007 | Mayse | |
| 2008/0077074 A1 | 3/2008 | Keenan et al. | |
| 2008/0091143 A1 | 4/2008 | Taylor et al. | |
| 2008/0097386 A1 | 4/2008 | Osypka | |
| 2008/0125709 A1 | 5/2008 | Chang et al. | |
| 2008/0132847 A1 * | 6/2008 | Wing et al. | 604/167.05 |
| 2008/0147012 A1 | 6/2008 | Rome | |
| 2008/0171988 A1 | 7/2008 | Blanco | |
| 2008/0195031 A1 | 8/2008 | Kitani et al. | |
| 2008/0262410 A1 | 10/2008 | Jenson et al. | |
| 2008/0265561 A1 | 10/2008 | Buchanan et al. | |
| 2009/0005739 A1 * | 1/2009 | Hart et al. | 604/167.06 |
| 2009/0088823 A1 | 4/2009 | Barak et al. | |
| 2009/0163941 A1 | 6/2009 | Solem et al. | |
| 2009/0240204 A1 * | 9/2009 | Taylor et al. | 604/167.03 |
| 2009/0306697 A1 * | 12/2009 | Fischvogt | 606/185 |
| 2010/0274193 A1 * | 10/2010 | Patton et al. | 604/167.01 |
| 2011/0224642 A1 * | 9/2011 | Fojtik | 604/500 |

FOREIGN PATENT DOCUMENTS

| | | |
|---|---|---|
| DE | 20 2007 006190 U1 | 8/2007 |
| EP | 2047809 A1 | 4/2009 |

\* cited by examiner ations to provide a fluid-tight seal when a pressure inside the access apparatus is greater than a pressure external thereof.

The present disclosure provides a zero closure valve that is adapted to connect to an access apparatus configured to provide access into an abdominal cavity of a patient. A check-valve is operably associated with the zero-closure valve and is in fluid communication with a longitudinal passage associated with an access member of the access apparatus and an insufflation port operably associated with the access member. The check-valve is configured to provide a fluid-tight seal when a pressure inside the access apparatus is greater than a pressure external thereof.

ACCESS APPARATUS INCLUDING INTEGRAL ZERO-CLOSURE VALVE AND CHECK VALVE

CROSS REFERENCE TO RELATED APPLICATION

The present application claims the benefit of and priority to U.S. Provisional Application Ser. No. 61/305,635 filed on Feb. 18, 2010, the entire contents of which are incorporated herein by reference.

BACKGROUND

1. Technical Field

The present disclosure relates to an access apparatus and, more particularly, to an access apparatus that includes an integral zero-closure valve and check valve for an insufflation port.

2. Description of Related Art

In laparoscopic procedures, clinicians perform surgery in the interior of the abdomen through a small incision, and in endoscopic procedures, clinicians conduct surgery in any hollow viscus of the body through a narrow tube or cannula inserted through a small entrance incision in the skin. In certain instances, one or more insufflation ports are operably associated with the narrow tube or cannula and are configured to provide a pressurized gas, e.g., $CO_2$, into the abdomen after the narrow tube or cannula is inserted into the incision and secured to a patient, thus creating a pneumoperitoneum. The gas provides a positive pressure that raises the inner body wall away from internal organs, thereby providing the surgeon with an operating space. By creating the operating space, the clinician avoids unnecessarily contacting the organs with the instruments inserted through the cannula assembly.

Typically, the one or more insufflation ports include one or more components, such as, for example, intricate manual valves, caps, stopcocks, external tubes and the like, that are configured to maintain the pneumoperitoneum and control for insufflation gas flow. As can be appreciated, the aforementioned components, e.g., intricate valves, increase the cost of manufacture of the insufflation port and/or access apparatus.

Accordingly, it may prove advantageous to provide an access apparatus that includes an easy to manufacture component that is configured to maintain the pneumoperitoneum and control for insufflation gas flow.

SUMMARY

The present disclosure provides an access apparatus for use in surgical procedures. The access apparatus includes an access member that defines a longitudinal axis and has a longitudinal passage that provides entry to an abdominal cavity of a patient. The longitudinal passage is adapted to permit passage of a surgical instrument utilized in performing a surgical procedure. A housing includes a proximal end defining an opening in communication with the longitudinal passage of the access member to permit passage of the surgical instrument. A zero-closure valve is disposed within the housing and adjacent the longitudinal passage. The zero-closure valve is configured to provide a substantially fluid-tight seal in the absence of the surgical instrument inserted therethrough. A check-valve is operably associated with the zero-closure valve and is in fluid communication with the longitudinal passage and an insufflation port operably associated with the access member. The check-valve is configured

BRIEF DESCRIPTION OF THE DRAWINGS

Various embodiments of the present disclosure are described herein with reference to the drawings wherein.

DETAILED DESCRIPTION

The access apparatus of the present disclosure provides a substantially fluid-tight seal between a body cavity of a patient and the outside atmosphere. The access apparatus of the present disclosure is configured to receive surgical instruments of varying diameters. Included among the various procedures contemplated by the present disclosure are endoscopic, laparoscopic, arthroscopic, orthopedic, etc.

The access apparatus of the present disclosure contemplates the introduction of various types of instrumentation during the particular procedure. Examples of instrumentation include, but are not limited to, clip appliers, graspers, dissectors, retractors, staplers, laser probes, photographic devices, endoscopes and laparoscopes, tubes, anchors, anchor drives, etc. Such instruments will collectively be referred to as "instruments" or "instrumentation" or "surgical objects."

In the following description, as is traditional, the term "proximal" refers to the portion of the device closer to the operator while the term "distal" refers to the portion of the device farther from the operator.

Figure 1:
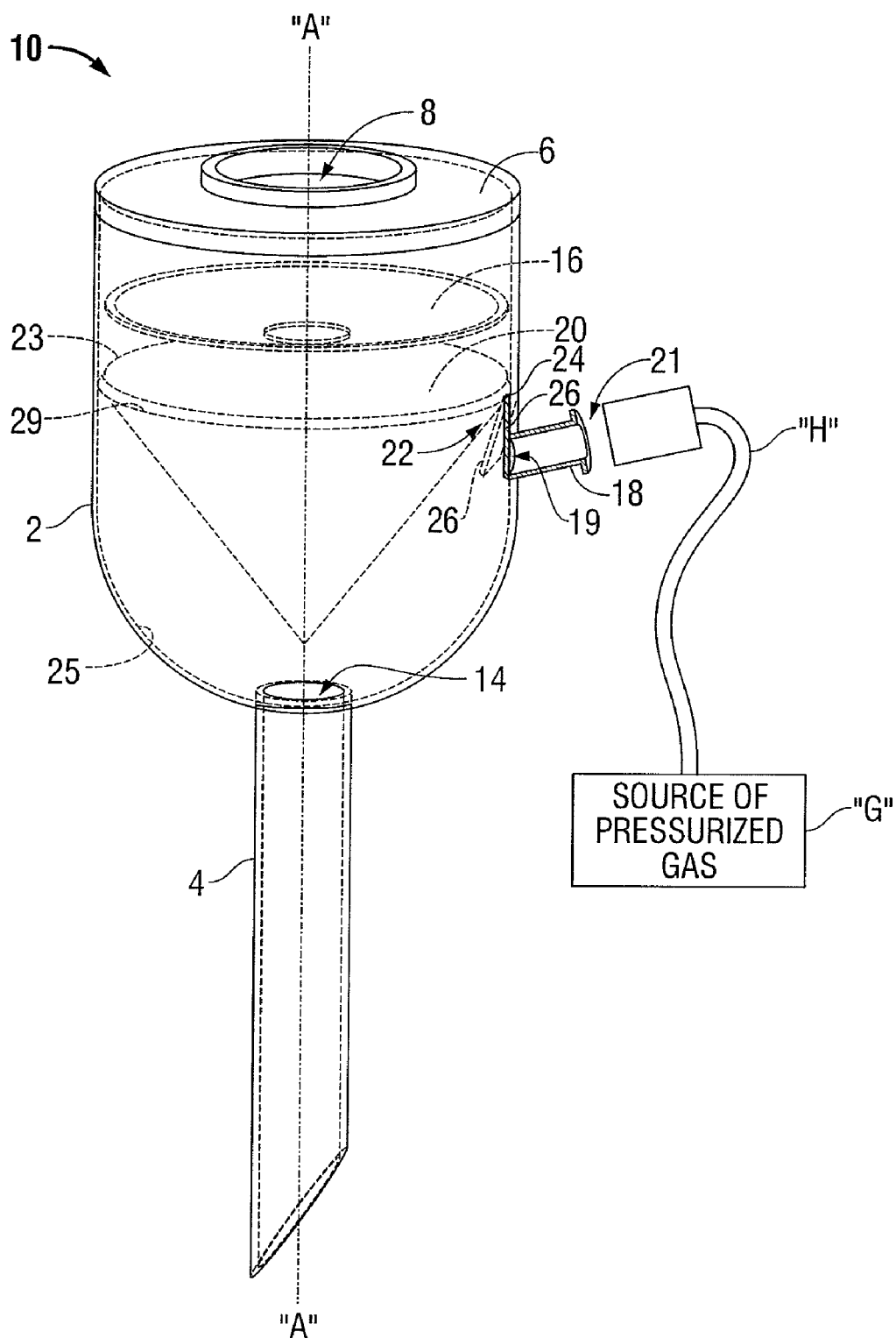
FIG. 1 is a perspective view of an access apparatus including an integral zero-closure valve and check valve according to an embodiment of the present disclosure.
Figure 2:
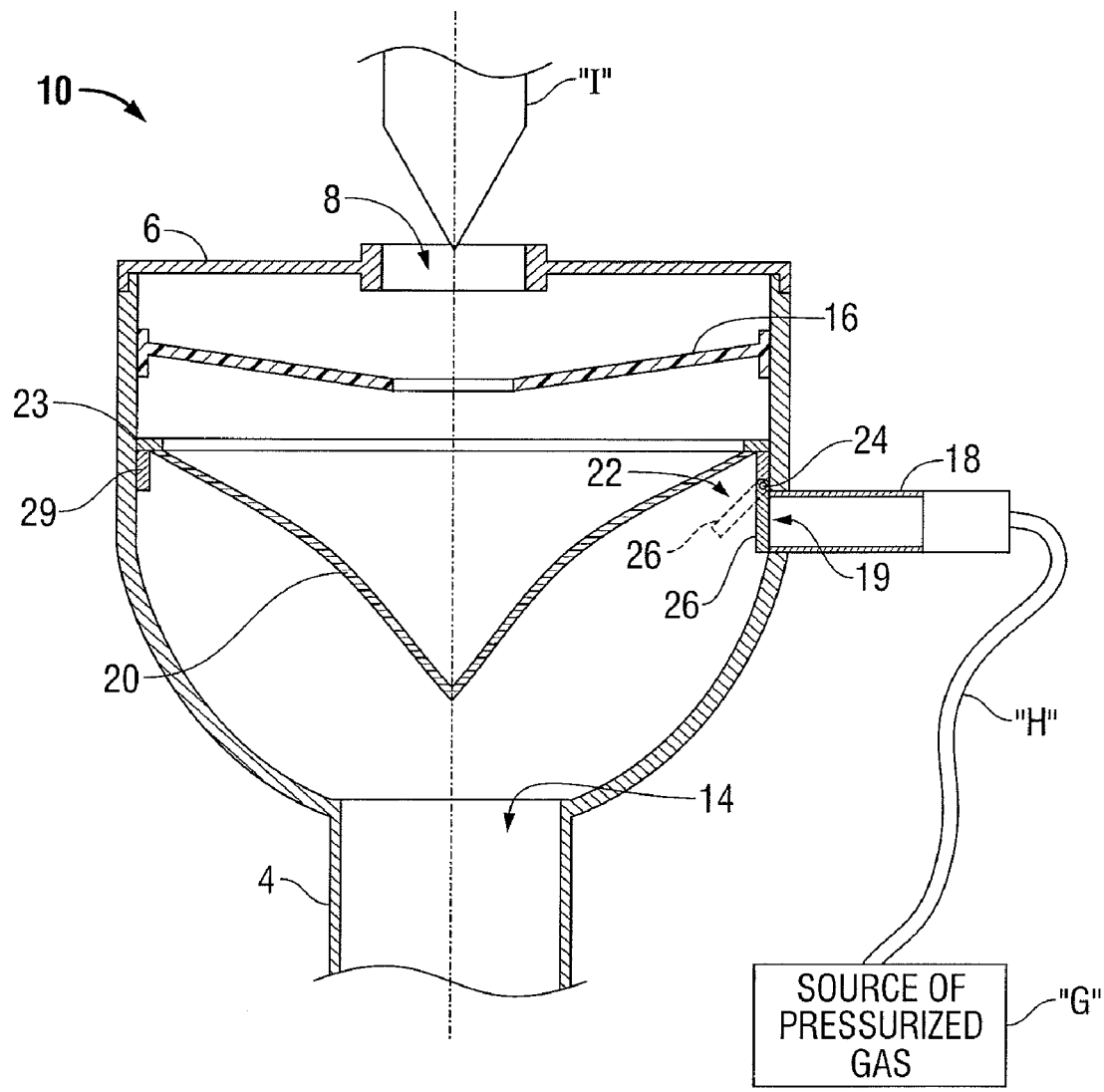
FIG. 2 is a side cross-sectional view of a proximal end of the access apparatus depicted in FIG. 1.

With reference to FIGS. 1 and 2, and initially with reference to FIG. 1 an access apparatus 10 is shown. Access apparatus 10 and operative components associated therewith may be formed from any suitable material, e.g., a biocompatible material that is made from an elastomeric material. Access apparatus 10 defines a longitudinal axis "A" and includes a housing 2 and an access member 4. A proximal end 6 of housing 2 includes an opening 8 and access member 4 defines a longitudinal passageway 14. Opening 8 and longitudinal passageway 14 are generally aligned with respect to the longitudinal axis "A" to permit passage of surgical objects such as instruments "I" (FIG. 2) utilized in connection with the procedure.

An insufflation port 18 of suitable proportion is operably coupled to the housing 2 via one or more suitable coupling methods including but not limited to a press fit or friction fit connection, soldering brazing, welding etc. In the illustrated embodiment, insufflation port 18 is monolithically formed with the housing 2. The insufflation port 18 serves as an intermediary interface that provides fluid communication between the access apparatus 10 and a source of insufflation gas "G." More particularly, a distal end of a hose "H" is operably coupled to the source of pressurized gas "G" and a proximal end of the hose "H" operably couples to the access apparatus 10 via one or more suitable coupling methods, e.g., a Luer type fitting or the like. In certain instances, the source of pressurized gas may be directly coupled, via a syringe, to the insufflation port 18. Insufflation port 18 includes open proximal and distal ends 19 and 21, respectively, that are of suitable proportion.

Access apparatus 10 includes a duck bill or zero-closure valve 20 that is disposed within the housing 2 and adjacent the longitudinal passageway 14. More particularly, zero-closure valve 20 securely affixes to an interior wall 25 of the housing 2 by known fixation methods. In one particular embodiment, the zero-closure valve 20 includes a generally circular flange 23 (FIG. 1) that rests upon a corresponding ledge or shelf 29, as best seen in FIG. 2, that is operably disposed on the interior wall 25 of the housing 2. More particularly, the ledge 29 substantially extends along a circumference of the interior wall 25 of the housing 2. In the illustrated embodiment, a gap or break in the ledge 29 is disposed adjacent the flange 23 of the zero-closure valve 20. In an assembled configuration, flange 23 rests on the ledge 29 such that the zero-closure valve 20 is maintained in a substantially fixed position. Zero-closure valve 20 tapers distally and inwardly to a sealed configuration, as best seen in FIG. 1. As such, zero-closure valve 20 is configured to provide a substantially fluid-tight seal in the absence of a surgical instrument "I" inserted therethrough, as is conventional in the art.

A check-valve 22 portion (check-valve 22) is operably associated with the zero-closure valve 20 and is configured to provide a fluid-tight seal when a pressure inside the access apparatus is greater than a pressure external thereof (FIGS. 1 and 2). In the illustrated embodiment, check-valve 22 is integrally formed with the zero-closure valve 20. More particularly, the check-valve 22 is monolithically formed with the zero-closure valve 20. In the illustrated embodiment, the check-valve 22 is operably disposed adjacent the flange 23 and the gap or break associated with the ledge 29. It should be recognized that while the present invention is illustrated and described herein as having the check valve 22 be associated with, e.g., formed as a single piece with, the zero-closure valve 20, other embodiments are contemplated in which the check valve 22 is associated with, e.g., formed as a single piece with, components of the access apparatus 10 other than the zero-closure valve 20. For example, in other embodiments, the check valve 22 may be associated with, e.g., formed as a single piece with, the instrument seal 16. However, having the check valve 22 be associated with, e.g., formed as a single piece with, the zero-closure valve 20 may have the advantage that insufflation fluid is introduced at a point that is distal relative to any seals/valves, thereby permitting the free flow of such insufflation fluid irrespective of whether such seals/valves are in the open or closed positions and irrespective of whether an instrument is present therein.

Check-valve 22 includes a generally elongated or "flapper" portion 26 (flapper 26) that is dimensioned to substantially, if not entirely, cover the open proximal end 19 of the insufflation port 18 when the flapper 26 is pressed against the interior wall 25 of the housing 2 adjacent the open proximal end 19 of the insufflation port 18. In an assembled configuration, the flapper 26 is positioned within the gap or break associated with the ledge 29. Positioning the flapper 26 within the gap or break assists in providing a fluid-tight seal when the flapper 26 is pressed against the interior wall 25 of the housing 2. Flapper 26 is configured to move radially inward (shown in phantom in FIGS. 1 and 2) when a pressure outside the access apparatus 10 is greater than a pressure inside the access apparatus 10. To this end, flapper 26 may be coupled to the zero-closure valve 20 via one or more suitable hinge interfaces and/or configurations. In the embodiment shown in FIG. 1, a hinge portion 24 couples the flapper 26 to the zero-closure valve 20. In this embodiment, the hinge portion 24 is made from the same elastomeric material from which the zero-closure valve 20 and flapper 26 are made, e.g., the zero-closure valve 20 and flapper 26 are monolithically/integrally formed such that the hinge portion 24 is merely a region of material between the zero-closure valve 20 and flapper 26 which acts as a hinge when the flapper 26 is moved relative to the zero-closure valve 20, e.g., it is a living hinge.

Alternatively, as shown in FIG. 2, the hinge portion 24 or portions thereof may be made from a material that is different from the material from which the zero-closure valve 20 and/or the flapper 26 are made. For example, in certain embodiments, the hinge portion 24 may incorporate a hinge pin and may be made from a material, e.g., an elastomeric material, that is more or less rigid (e.g., to achieve a desired radially flexing or moving of the flapper portion 26 for a given amount of change in pressure "ΔP") than the elastomeric material from which the zero-closure valve 20 and/or flapper 26 are made.

Figure 3:
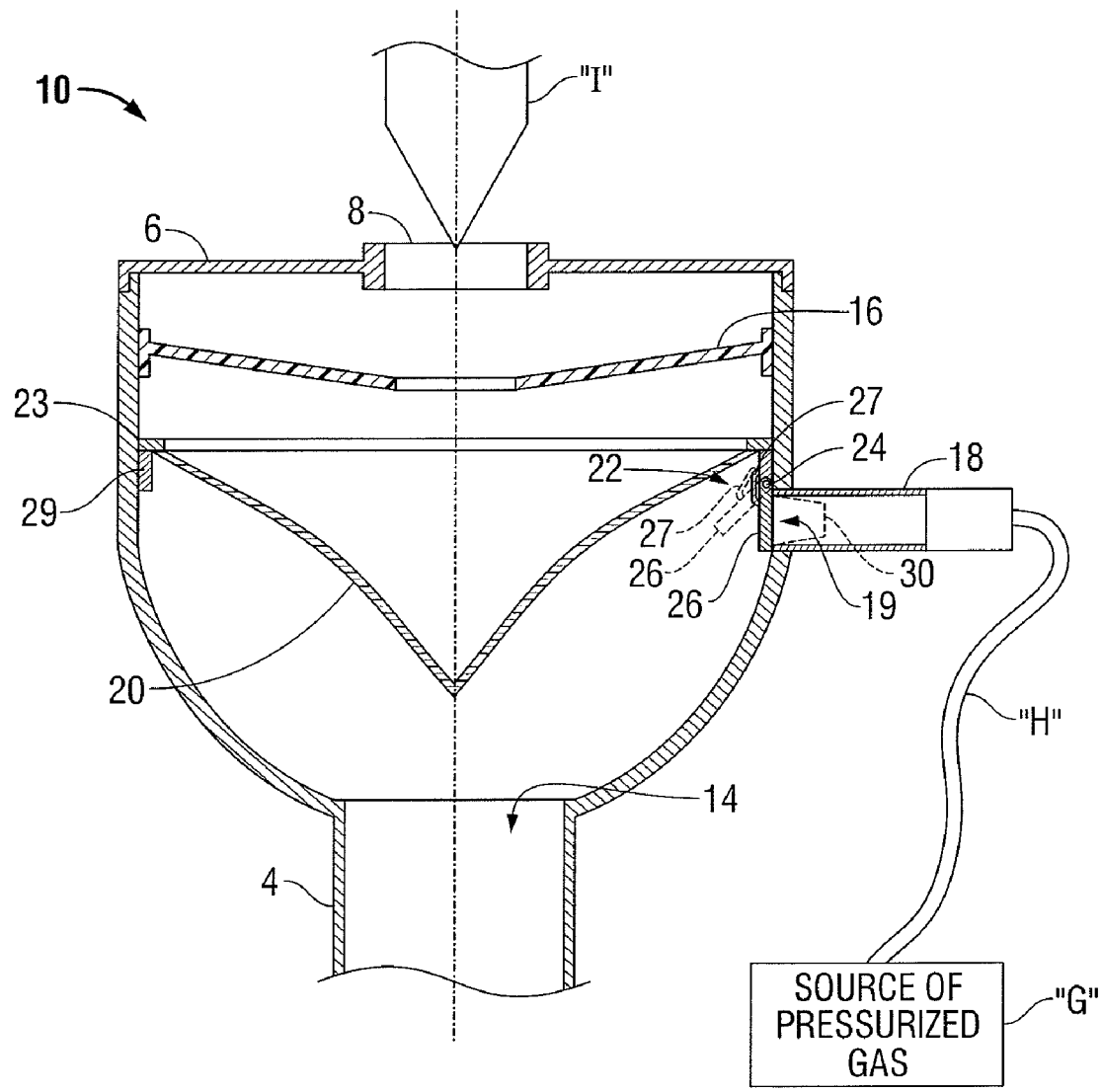
FIG. 3 is a side cross-sectional view of a proximal end of the access apparatus according to an alternate embodiment of the present disclosure.

In embodiments, a resilient member may be operably associated with the zero-closure valve 20 and/or check-valve 22 (FIG. 3). For example, a spring 27 may be operably associated with the check-valve to assist in maintaining a fluid-tight seal when a pressure inside the access apparatus is greater than a pressure external thereof. The spring 27 may be any suitable spring known in the art including, but not limited to a leaf spring, a torsion spring, a coil spring, etc. In the embodiment illustrated in FIG. 3, the spring 27 is a torsion spring 27 that is operably coupled to the flapper 26 and a portion of the zero-closure valve 20.

In certain embodiments, the access apparatus 10 may include one or more instrument seals 16 (see FIGS. 1 and 2, for example) disposed within the housing 2 and adjacent longitudinal passageway 14 and in mechanical cooperation with housing 2. Instrument seal 16 is configured to create a substantially fluid-tight seal around an instrument "I" introduced through the seal 16. One suitable instrument seal is disclosed in commonly assigned U.S. Pat. No. 6,702,787 to Racenet, the entire contents of which disclosure is incorporated by reference herein.

From the foregoing and with reference to the various figure drawings, those skilled in the art will appreciate that certain modifications can also be made to the present disclosure without departing from the scope of the same. For example, flapper 26 may include a raised portion 30, e.g., a detent 30, which is configured and proportioned to "plug" the open proximal end 19 of the insufflation port 18 when the flapper 26 is pressed against the interior wall of the housing 2. Additionally or alternatively, the proximal end 19 of the insufflation port 18 may have a shape, e.g., sloped surfaces, that are configured to engage the raised portion 30 of the flapper 26 and thereby receive the detent 30. For illustrative purposes, the detent 30 is shown in phantom. Detent 30 assists in maintaining the flapper 26 and opening 19 in a fluid-tight sealed engagement with each other, when sealing therebetween is desired. More particularly, the integrity of the fluid-tight seal between the flapper 26 and insufflation port 18 may be increased because of the configuration of flapper 26 and detent 30. That is, the detent 30 "plugs" the open proximal end 19 of the insufflation port 18.

It should be recognized that, in alternative embodiments, the detent 30 may be located on or adjacent to the proximal end 19 of the insufflation port, and that the shape, e.g., sloped surfaces, for engaging same may instead be located on the flapper 26. Additionally, in certain embodiments, the detent 30 and/or an interior of the insufflation port 18 adjacent the open proximal end 19 may be made from or coated with a lubricous material (e.g., tetrafluoroethylene) that is designed to decrease the coefficient of static friction between the detent 30 and the interior of the insufflation port 18 adjacent the open proximal end 19.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An access apparatus for use in surgical procedures, the access apparatus comprising:
    an access member defining a longitudinal axis and having a longitudinal passage that provides entry to an abdominal cavity of a patient, the longitudinal passage being adapted to permit passage of a surgical instrument utilized in performing a surgical procedure;
    a housing including a proximal end defining an opening in communication with the longitudinal passage of the access member to permit passage of the surgical instrument; and
    a zero-closure valve disposed within the housing and adjacent the longitudinal passage, the zero-closure valve configured to provide a substantially fluid-tight seal in the absence of the surgical instrument inserted therethrough, the zero-closure valve including a check-valve integrally formed therewith, the check-valve in fluid communication with the longitudinal passage and an insufflation port operably associated with the access member, wherein the check-valve is configured to provide a fluid-tight seal when a pressure inside the access apparatus is greater than a pressure external thereof,
    wherein the check-valve includes a flapper portion hinged to the zero-closure valve, the flapper portion and zero-closure valve formed with a region of material therebetween that functions as a living hinge configuration when the flapper portion is moved relative to the zero-closure valve.

2. An access apparatus according to claim 1, wherein a detent is operably disposed on the flapper portion and configured to provide increased fluid tight integrity of the fluid-tight seal in the absence of fluid through the check-valve.

3. An access apparatus according to claim 1, wherein a spring is operably associated with the check-valve and configured to assist in maintaining a fluid tight seal between the flapper portion and the insufflation port in the absence of fluid therethrough and when a pressure inside one of the abdominal cavity and the access apparatus is greater than a pressure external thereof.

4. An access apparatus according to claim 3, wherein the spring is of the type selected from the group consisting of a torsion spring, leaf spring and coil spring.

5. An access apparatus according to claim 1, wherein at least a portion of the zero-closure valve and the check-valve are made from an elastomeric material.

6. An access apparatus according to claim 1, wherein the access apparatus includes an instrument seal.

7. A zero closure valve adapted to connect to an access apparatus configured to provide access into an abdominal cavity of a patient, comprising:
    a check-valve integrally formed with the zero-closure valve and, the check-valve in fluid communication with a longitudinal passage and an insufflation port operably associated with the access member, wherein the check-valve is configured to provide a fluid-tight seal when a pressure inside the access apparatus is greater than a pressure external thereof,
    wherein the check-valve includes a flapper portion hinged to the zero-closure valve, the flapper portion and zero-closure valve formed with a region of material therebetween that functions as a living hinge configuration when the flapper portion is moved relative to the zero-closure valve.

8. An access apparatus according to claim 7, wherein a detent is operably disposed on the flapper portion and configured to provide increased fluid tight integrity of the fluid-tight seal in the absence of fluid through the check-valve.

9. An access apparatus according to claim 7, wherein a spring is operably associated with the check-valve and configured to assist in maintaining a fluid-tight seal between the flapper portion and the insufflation port in the absence of fluid therethrough and when a pressure inside one of the abdominal cavity and the access apparatus is greater than a pressure external thereof.

10. An access apparatus according to claim 9, wherein the spring is of the type selected from the group consisting of a torsion spring, leaf spring and coil spring.

11. An access apparatus according to claim 7, wherein at least a portion of the zero-closure valve and the check-valve are made from an elastomeric material.

12. An access apparatus according to claim 7, wherein the access apparatus includes an instrument seal.

* * * * *